(12) United States Patent
Miller

(10) Patent No.: US 10,226,322 B2
(45) Date of Patent: *Mar. 12, 2019

(54) JUGULAR FEMORAL VENA CAVA FILTER SYSTEM

(71) Applicant: C.R. Bard, Inc., Murray Hill, NJ (US)

(72) Inventor: Jonathan D. Miller, Mesa, AZ (US)

(73) Assignee: C.R. BARD, INC., Murray Hill, NJ (US)

( * ) Notice: Subject to any disclaimer, the term of this patent is extended or adjusted under 35 U.S.C. 154(b) by 282 days.

This patent is subject to a terminal disclaimer.

(21) Appl. No.: 15/206,858

(22) Filed: Jul. 11, 2016

(65) Prior Publication Data

US 2017/0007389 A1 Jan. 12, 2017

Related U.S. Application Data

(63) Continuation of application No. 13/954,759, filed on Jul. 30, 2013, now Pat. No. 9,393,095, which is a continuation of application No. 12/519,702, filed as application No. PCT/US2007/087760 on Dec. 17, 2007, now Pat. No. 8,518,072.

(60) Provisional application No. 60/870,498, filed on Dec. 18, 2006.

(51) Int. Cl.
*A61F 2/01* (2006.01)

(52) U.S. Cl.
CPC ........... *A61F 2/01* (2013.01); *A61F 2002/011* (2013.01); *A61F 2002/016* (2013.01); *A61F 2210/0014* (2013.01); *A61F 2230/005* (2013.01)

(58) Field of Classification Search
CPC .......... A61F 2/0095; A61F 2/01; A61F 2/013; A61F 2/1691; A61F 2002/011; A61F 2002/016; A61F 2002/018; A61B 17/122; A61B 17/865; A61B 2017/00362; A61B 2017/0416; A61B 2017/1205; A61B 2017/12095

See application file for complete search history.

(56) References Cited

U.S. PATENT DOCUMENTS

| 4,425,908 A | 1/1984 | Simon |
| 4,832,055 A | 5/1989 | Palestrant |
| 4,994,069 A | 2/1991 | Ritchart et al. |
| 5,147,379 A | 9/1992 | Sabbaghian et al. |
| 5,160,342 A | 11/1992 | Reger et al. |
| 5,188,616 A | 2/1993 | Nadal |
| 5,370,657 A | 12/1994 | Irie |
| 5,836,969 A | 11/1998 | Kim et al. |
| 6,126,673 A | 10/2000 | Kim et al. |
| 6,258,026 B1 | 7/2001 | Ravenscroft et al. |

(Continued)

FOREIGN PATENT DOCUMENTS

FR 0403044 3/2004

*Primary Examiner* — Todd Scherbel
(74) *Attorney, Agent, or Firm* — Garvey, Smith & Nehrbass, Patent Attorneys, LLC; Seth M. Nehrbass; Charles C. Garvey, Jr.

(57) ABSTRACT

An embolus filter introducer system has a symmetric introducer sheath with a filter inside. The introducer sheath can be attached at either end to a deployment actuator. The deployment actuator can thereby be used to push the filter out of the introducer sheath. Since the sheath can be oriented in a selectable direction, so can the filter, allowing the sheath to be introduced via a jugular or femoral approach to the vena cava.

20 Claims, 3 Drawing Sheets

(56) References Cited

U.S. PATENT DOCUMENTS

| | | |
|---|---|---|
| 6,273,901 B1 | 8/2001 | Whitcher et al. |
| 6,383,193 B1 | 5/2002 | Cathcart et al. |
| 6,589,266 B2 | 7/2003 | Whitcher et al. |
| 6,793,665 B2 | 9/2004 | McGuckin, Jr. et al. |
| 7,018,401 B1 | 3/2006 | Hyodoh et al. |
| 7,047,068 B2 | 5/2006 | Haissaguerre |
| 7,314,477 B1 | 1/2008 | Ravenscroft et al. |
| 7,794,473 B2 | 9/2010 | Tessmer et al. |
| 7,879,090 B2 | 2/2011 | Pynson |
| 8,518,072 B2 * | 8/2013 | Miller .................. A61F 2/01 606/200 |
| 9,393,095 B2 * | 7/2016 | Miller .................. A61F 2/01 |
| 2003/0060843 A1 | 3/2003 | Boucher |
| 2003/0093106 A1 | 5/2003 | Brady et al. |
| 2003/0229374 A1 | 12/2003 | Brady et al. |
| 2005/0080447 A1 | 4/2005 | McGuckin, Jr. et al. |
| 2005/0080449 A1 | 4/2005 | Mulder |
| 2005/0234503 A1 | 10/2005 | Ravenscroft et al. |
| 2005/0288703 A1 | 12/2005 | Beyer et al. |
| 2006/0030875 A1 | 2/2006 | Tessmer |
| 2006/0041271 A1 | 2/2006 | Bosma et al. |
| 2009/0131970 A1 | 5/2009 | Chanduszko et al. |

\* cited by examiner

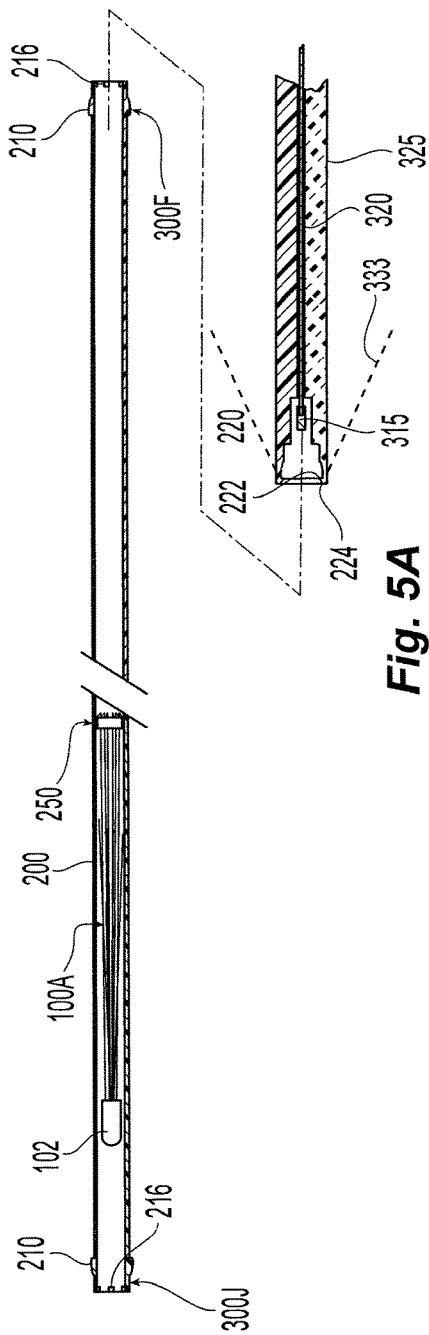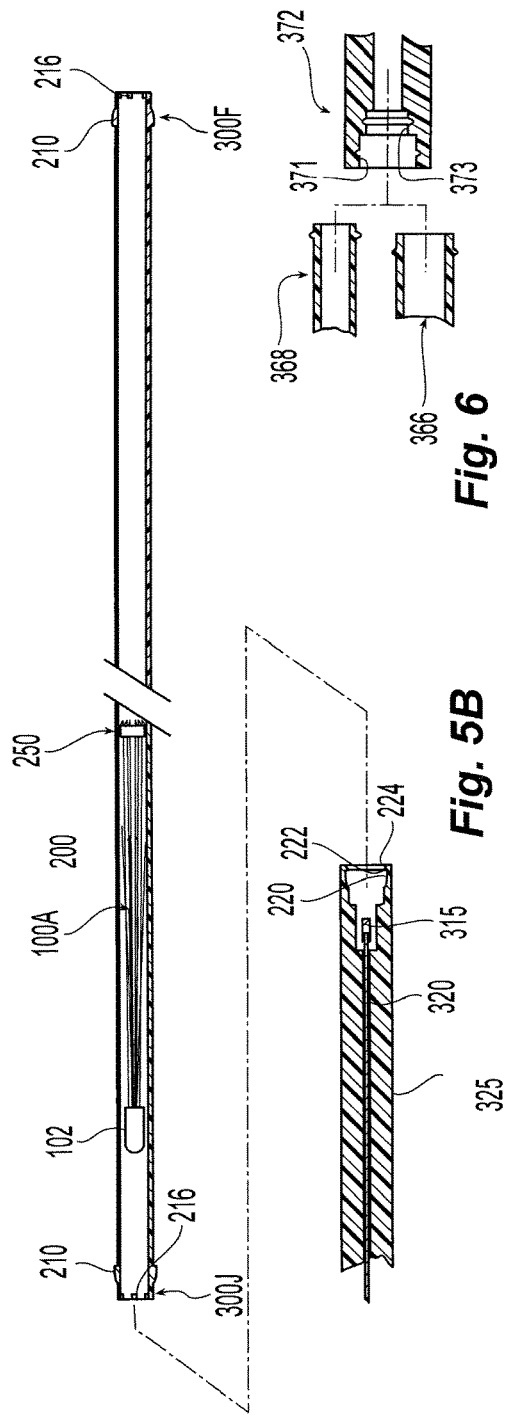

JUGULAR FEMORAL VENA CAVA FILTER SYSTEM

PRIORITY DATA AND INCORPORATION BY REFERENCE

This application claims the benefit of priority to U.S. Provisional Patent Application No. 60/870,498, filed Dec. 18, 2006, which is incorporated by reference in its entirety.

TECHNICAL FIELD

The invention relates to a filter device that can be placed via an introducer sheath delivery system in a vessel of a mammalian body to reduce the risk of embolisms. The invention further relates to features that allow the same filter and introducer sheath assembly to be used to deploy a filter from a jugular or femoral access. Further features permit the filter to be pre-sealed within a reorientable delivery introducer sheath.

BACKGROUND ART

Inferior vena cava filters, also called IVC filters or Greenfield filters, are medical devices that are implanted into the inferior vena cava to prevent pulmonary emboli. They work by trapping emboli while still permitting the flow of blood, thereby preventing an embolus from sealing off a vessel. IVC filters are used if anticoagulation is ineffective or contraindicated.

IVC filters are inserted via the blood vessels (i.e., placed endovascularly). Known filters can be compressed into thin introducer sheaths permitting access to the venous system via the femoral vein or the internal jugular vein. An introducer sheath is guided into the IVC using fluoroscopic guidance. The filter is pushed through the introducer sheath and deployed into the desired location. IVC filters are usually positioned just below the junction of the IVC and the lowest renal vein.

A variety of different kinds of filter designs are known. Some of these are symmetrical and can be delivered through both jugular and femoral accesses. The following are some examples.

US Patent Publication No. 2003/0060843 shows a filter which has an umbrella-like structure to capture emboli with struts that connect the filter to a catheter which has a capsule on its end to hold the filter in a collapsed configuration. The catheter and capsule remain in place while the filter is in use so no vessel wall-holding features are required. The filter readily collapses as it is drawn into the capsule since there are no extensions to get in the way.

U.S. Pat. No. 6,793,665 and US Patent Publication No. 2005/0080447 show a filter with one or more meandering filaments that define a self-expanding structure that can be drawn into a catheter. The pressure of the meandering filament(s) against the vessel wall prevents the filter from migrating. In one embodiment, the filter is symmetrical and can be placed through a jugular or femoral access.

US Patent Publication No. 2005/0288703 shows a filter with a capture part with obliquely extending struts stemming from a hub which is attached at the strut endpoints to a series of V-shaped extensions that are displaced in a flow direction from the ends of the struts. The ends of the extensions have sharp tips that engage the vessel wall to prevent movement.

US Patent Publication No. 2006/0041271 shows a filter with a cover that can be placed through a catheter. The filter is self-expanding from a compressed shape that is assumed by it when it is inside the catheter. A cover over those portions of the filter that would otherwise contact the vessel wall reduces pressure on the wall. The cover also helps to resist incorporation of the filter into the vessel wall by endothelialization. Oppositely-directed tips engage the wall to prevent movement.

U.S. Pat. No. 5,370,657 shows a filter in which two self-expanding corolla elements are interlaced in opposite directions. At the center of each corolla is a hook that can be approached from opposite ends by loops that engage each hook to pull the corollas apart. The corollas are held together by a resilient element that breaks when the two corollas are pulled apart, allowing each corolla to be drawn into, and collapsed within, a sheath for retrieval.

U.S. Pat. Nos. 5,836,969 and 6,126,673 show a filter with multiple corollas that can assume a very small size when compressed within a catheter before deploying. The filter is made of filter-wires that extend generally upstream from a central region of connection, free ends that engage the vessel wall.

U.S. Pat. Nos. 6,273,901 and 6,589,266 show a filter that is similar to that of U.S. Pat. No. 5,370,657, but the wires making up the corollas follow much more complex trajectories. Also, an embodiment with hooks on the corolla hubs is shown, but they are not explained in the patent.

U.S. Pat. No. 7,018,401 shows a filter with oppositely-directed dome portions that can have hooks at the tops of their domes. The patent says the hooks can be used for retrieval. The domes are flexible.

There may be various reasons for preferring asymmetric filter designs over symmetric ones. The latter tend to be longer, for instance. It is possible the sizes of the introducer sheaths may need to be longer, depending on the particular design. Filters are generally prepackaged in the introducer sheath for at least two reasons. The first is that it is desirable for filters to be highly compressed to fit into a thin introducer sheath, which is a difficult task to perform so it is usually done under controlled conditions as a final step in manufacturing. Thus, filters are delivered pre-fitted within the introducer sheath. The second reason filters are pre-installed in the introducer sheath is for sterility. Sealed and sterilized while within the introducer sheath, the risk of contamination is greatly reduced. It is desirable for a filter of asymmetric design to be deliverable through femoral and jugular accesses without the need for separate delivery systems.

DISCLOSURE OF INVENTION

Briefly, An embolus filter introducer system has a symmetric introducer sheath with a filter inside. The introducer sheath can be attached at either end to a deployment actuator. The deployment actuator can thereby be used to push the filter out of the introducer sheath. Since the sheath can be oriented in a selectable direction, so can the filter, allowing the sheath to be introduced via a jugular or femoral approach to the vena cava.

An embodiment of a jugular-femoral filter delivery system has a reversible introducer sheath that contains a filter of asymmetric design. That is, the filter has a cranial end which is intended to be oriented in a cranial direction and a caudal end which is intended to be oriented in a caudal direction. The reversible introducer sheath contains a filter and connects to a delivery device at selectable opposite ends thereof. This permits the filter to be pushed out either end of the introducer sheath. Engagement portions of the filter may be retained by a spline cap that keeps the engagement elements from impeding movement of the filter through the introducer sheath. In an embodiment, the engagement elements are legs with hooks at their ends.

The spline cap is guided by slides that run from one end of the introducer sheath to the other. Abutments on both ends of the introducer sheath prevent loss of the spline cap into the body during deployment. The filter is loaded with the legs in the spline cap. The spline cap is moveable, so it will be positioned on the jugular side of the sheath with the filter legs retained by it. The introducer sheath will then be connected via snap-fit to a pusher assembly. A pusher which is almost the size of the spline cap is advanced through the introducer sheath so that is pushes the filter out of the introducer sheath. In the femoral approach, the hooks bend until the filter is released from the spline cap. In the jugular approach, the hooks are pushed beyond the spline cap. In either case, the spline cap is retained within the reversible introducer sheath by abutments at the ends of the sheath.

According to an embodiment, an embolus filter delivery device has a pusher assembly with a frame and a pusher member movable with respect to the frame. An introducer sheath has an embolus filter housed therein. The introducer sheath has engagement portions on either end thereof. Either of the introducer sheath engagement portions is connectable to the pusher assembly frame to allow the pusher member to move into the introducer sheath and push the filter out of it and such that the filter can be pushed out of the introducer sheath in either of two opposite directions.

Preferably, in the foregoing embodiment, the introducer sheath engagement portions and the pusher assembly frame are configured to provide a snap-fit connection between them to hold the introducer sheath to the pusher assembly. The introducer sheath preferably has a length that is sufficient to extend from a femoral access to a vena cava of a human.

The introducer sheath can have a length that is sufficient to extend from a jugular access to a vena cava of a human. Alternatively, the introducer sheath can extend only part of the length required with the pusher assembly making up the difference. The total length is preferably sufficient to extend from a standard femoral access of a human to the vena cava and the from a standard jugular access to the vena cava.

The embodiment is suited to a filter that has a longitudinal axis and which filter has an asymmetric shape with respect to the longitudinal axis. The filter would generally be oriented with respect to its cranial end and its caudal end when in position. The filter is configured to be pushed from either end by the pusher member. The filter may have engagement elements that are held by a spline cap. The spline cap is preferably slidable within the introducer sheath. The introducer sheath preferably has an internal surface with protruding portions that center the spline cap therewithin. Thus, the spline cap being centered can thereby prevent the engagement element ends from contacting the internal surface. This can ensure the filter can be pushed along the introducer sheath. Preferably, the introducer sheath is sealed by removable seals at either end of the introducer sheath.

The filter may have a hub and at least one corolla with axially and radially extending elements extending from the hub. The filter may have ends that are oriented such that one end is aimed in the cranial direction when deployed in a vena cava and the other is aimed in the caudal direction when deployed in a vena cava.

According to another embodiment, a method of delivering an embolus filter includes: choosing a jugular or femoral approach to place an embolus filter in a living host and deploying a filter using an introducer sheath oriented, with respect to a living host, in a direction corresponding to the chosen of the jugular or femoral approach. The deploying may include attaching an introducer sheath, which contains the embolus filter, to a deployment actuator at an end that corresponds to the chosen approach, the deployment actuator being used to push the filter out of the introducer sheath to deploy the filter. The introducer sheath may be attachable at either end to a deployment actuator and insertable into a living host at either end.

The deploying may further include attaching an introducer sheath, which contains the embolus filter, to a deployment actuator at an end that corresponds to the chosen approach, and inserting the introducer sheath into a living host beginning at the end of the introducer sheath opposite the end corresponding to the chosen approach, whereby the filter is oriented relative to the living host. Preferably, the deploying includes pushing the filter out of the introducer sheath.

The method may further include orienting the introducer sheath with respect to a deployment device and attaching it in one of two possible ways, each corresponding to a respective one of the femoral and jugular approaches.

In another embodiment, a sheath with first and second ends sealed at both ends with a vena cava filter within it. The filter and interior of the sheath are sterilized. The sheath is packaged with a delivery mechanism that can be attached to either end of the sheath to allow the filter to be deployed from the opposite end of the sheath by inserting the opposite end into a corresponding one of a jugular and venous access. The filter has a cranial end that is aligned with the sheath and, when deployed, must face the cranial end of the vena cava. Thus, choosing the end of the sheath to attach to the deployment mechanism and inserting the sheath via the opposite end, causes the filter to be inserted into the vena cava with a chosen orientation. In this way, the filter can always be placed with the filter cranial end facing the vena cava cranial end.

In yet another embodiment, a sheath for connection to a deployment actuator for introducing a filter. The sheath includes a tubular member having a first end and a second end. The tubular member includes an inner surface defining an interior space between the first and second ends for housing the filter. The sheath further includes first means for engaging a pusher assembly to provide for introduction of the filter from the second end and second means for engaging a pusher assembly to provide for introduction of the filter from the first end.

In any of the foregoing embodiments having a spline cap, the spline cap may have grooves that face radially outward. The filter engagement elements may be held by the spline cap while the spline cap grooves are held by protrusions on the inside of the introducer sheath. This prevents the spline cap from rotating, thereby preventing the legs from twisting.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIGS. 4A and 4B show cross-section of a portion of the structure in FIG. 3 illustrating the location and function of the spline cap according to two respective embodiments, one having a spline cap with no grooves and the other having grooves to engage ridges in the introducer sheath to prevent rotation of the spline cap and thereby to prevent twisting of the legs.

FIGS. 5A and 5B show alternative mating configurations of a reversible introducer sheath and a pusher assembly.

FIG. 6 shows an alternative fitting assembly in which the ends of a introducer sheath have different sizes.

MODE(S) OF CARRYING OUT THE INVENTION

An illustrative embodiment of a vena cava filter is shown and described in U.S. Pat. No. 6,258,026 for "Removable embolus blood clot filter and filter delivery unit" and U.S. Pat. No. 6,007,558 for "Removable embolus blood clot filter;" both of which are hereby incorporated by reference in their entireties herein. A similar vena cava filter is shown at 100 in FIGS. 1 and 2.

Figures 1, 2:
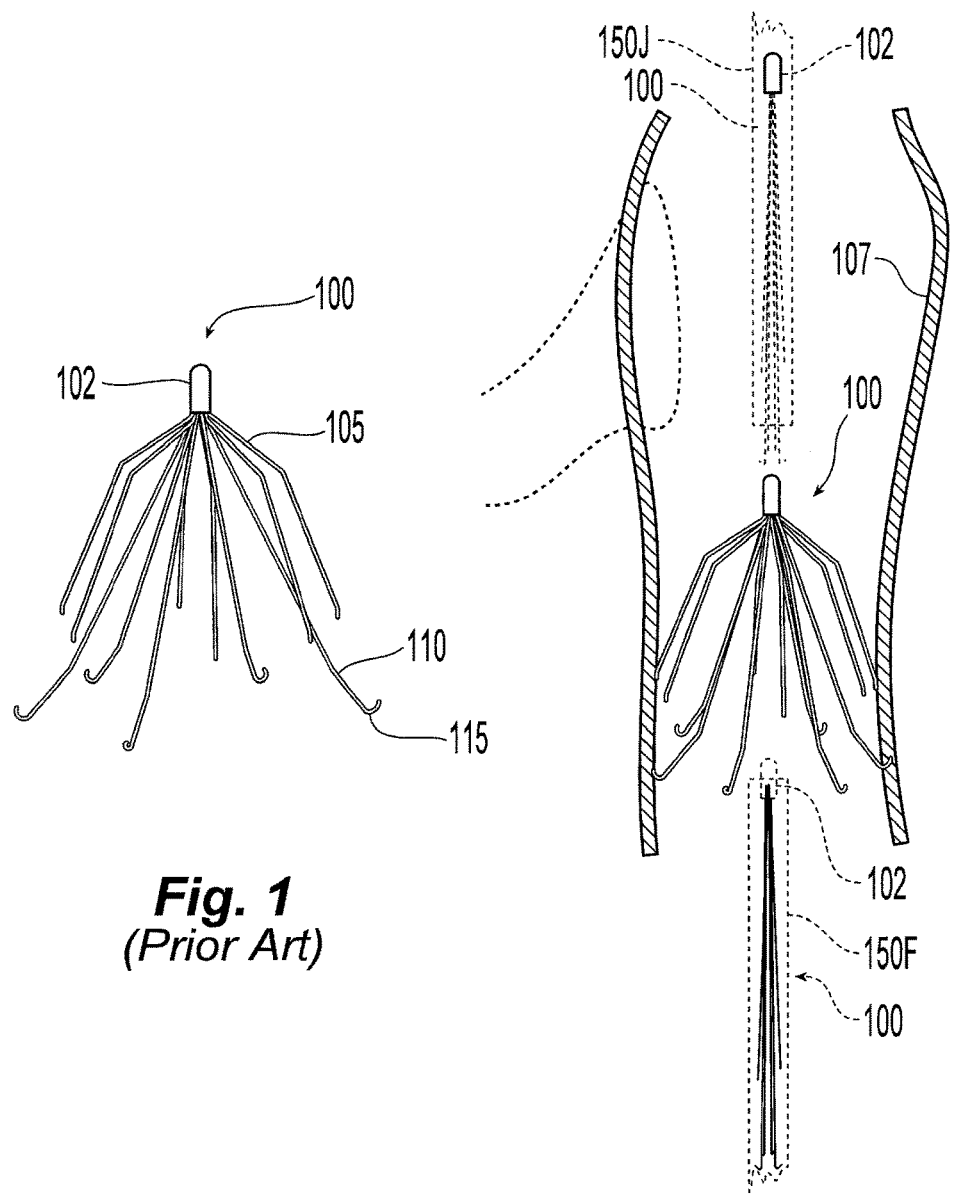
FIG. 1 shows an example of a filter of asymmetric design according to the prior art.
FIG. 2 shows the placement process of the filter of FIG. 1 using a femoral and a jugular approach according to the prior art.

Referring to FIGS. 1 and 2, the filter 100 is shown in an expanded state. Preferably, the filter is made of metal wires forming extension elements 105, 110 and held together by a hub 102 where they are joined, for example, by plasma welding. The wires are preferably made of shape memory alloy with a martensite phase that allows the wires to be straightened so as to enable insertion in a catheter and deployment therefrom. In the austenitic phase, the filter recovers to its expanded state, which is illustrated. Other details relating to the design can be found in the documents incorporated by reference above.

The filter 100 preferably has a double basket design with first extension elements 105 forming one basket and second extension elements 110 forming a second basket. Both the first extension elements 105 and second extension elements 110 engage the walls of the vena cava 107 after deployment. The second extension elements 110 preferably have hooked ends 115 that penetrate the vena cava 107 wall and prevent the filter 100 from moving downstream due to the frictional force of blood moving past it. As described in the above incorporated documents, preferably, the hooked ends 115 are configured to yield upon the application of a specified amount of force to ameliorate retrieval.

The filter 100 may be delivered by femoral or jugular access as illustrated by the introducer sheaths in FIG. 2, showing alternatively a sheath 150J in a jugular approach and a sheath 150F in a femoral approach. When the jugular approach is used, the filter 100 is pushed from the introducer sheath 150J with the basket concavity first and the hub 102 last. When the femoral approach is used, the filter 100 is pushed from the introducer sheath 150F with the basket concavity last and the hub 102 first. Accordingly, a different orientation of the filter 100 within the introducer sheath is required depending upon the approach. Prior to the inventor's development, two types of introducer sheaths 150J, 150F were required where the filter 100 was pre-sealed within the introducer sheath 150J, 150F in order to provide a sheath for each type of approach: (i) a sheath 150J and filter oriented for a jugular approach and (ii) a sheath 150F and filter oriented for the femoral approach.

Figure 3:
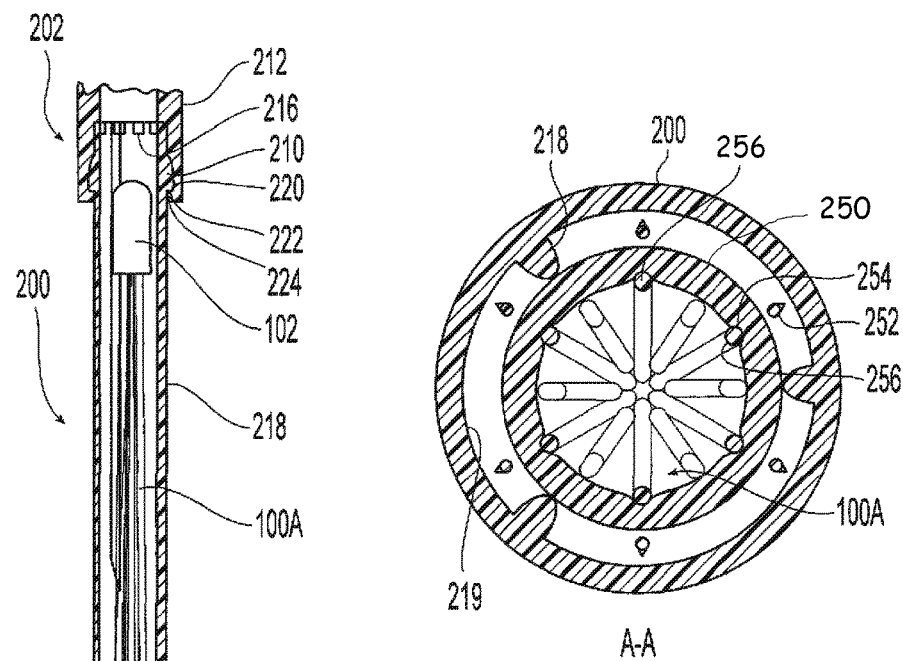
FIG. 3 shows a filter fitted in a reversible introducer sheath.

To reduce or otherwise eliminate the need for two types of introduction sheaths, the inventor has developed a single introducer sheath, with a preferably pre-installed filter, that can be used in either a jugular or a femoral approach. FIG. 3 shows an illustrative filter 100A loaded into an introducer sheath 200 having a preferred symmetric design to facilitate either a jugular or femoral approach. The introducer sheath 200 is a preferably tubular member having opposed ends 202. The tubular member 200 has an inner surface 219 defining an interior space for housing the filter 100. The ends 202 of the sheath 200 are preferably identical. Accordingly, only one end 202 is shown. The sheath end 202 is shown mated with the end of a pusher assembly 212 (also shown at 325 in FIGS. 5A and 5B discussed below) or other deployment actuator. The introducer sheath end 202 has a preferably snap fit protrusion 210 that engages a recess 220 with an edge 222 to seal and hold the introducer sheath 200 in the pusher assembly. Because of the symmetrical and preferably identical design of the introducer sheath ends 202, the sheath 200 can be reversed or interchangeable coupled at its ends 202 to a pusher assembly to appropriately orient the filter 100 for either a femoral or a jugular approach.

The introducer sheath 200 further preferably includes abutments 216 at its ends to prevent a spline cap 250, disposed about the extension elements of the filter 100, from moving beyond the ends 202 of the introducer sheath 200. The spline cap 250 maintains the extension elements of the filter in a radially collapsed configuration within the sheath 200 in order to minimize or eliminate frictional engagement between the interior surface of the sheath 200 and the filter 100.

Figure 4B:
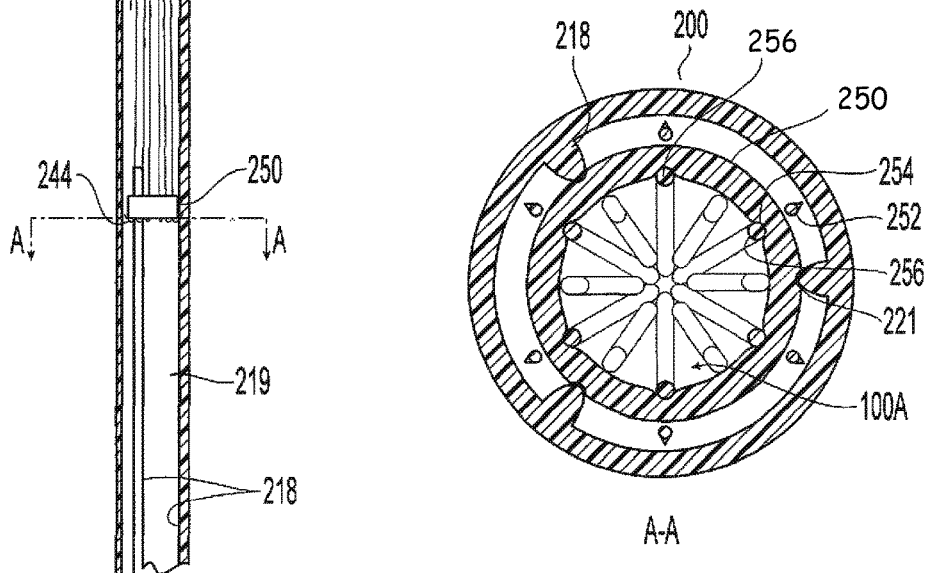

Referring to both FIGS. 3 and 4A, the spline cap 250 preferably has a generally cylindrical shape dimensioned so as to slide within the interior of the sheath 200. The interior surface of the introducer sheath 200 preferably includes one or more projections or rails 218 to engage and guide the spline cap 250 along the axial length of the sheath 200. More specifically, the spline cap 250 is guided by the rails 218 which further preferably center the spline cap 250 in spaced relation to most of the inner surface 219 of the introducer sheath 200. The spacing provides room for hooks 244 on the filter 100A. The hooks 244 are shown in section at 252 (only one is labeled, although six are shown). The filter 100A extension elements or legs 256 wrap around the spline cap 250 ending in the hooks 244. Recesses 254 may be formed in the spline cap 250 to hold the legs 256 in position with respect to it, the legs 256 being held by spring tension. FIG. 4B shows a cross-section of an alternate embodiment of the spline cap 250. Spline cap 250 preferably has grooves 221 that engage the rails 218 of the introducer sheath 200 to prevent the spline cap 250 from rotating. This in turn prevents twisting of the legs 256 of the filter 100.

Referring now to FIGS. 5A and 5B, to use the filter delivery system for a femoral approach, the introducer sheath 200 is connected to the pusher assembly 325 at a femoral end 300F such that the hub 102 is introduced first from the sheath. To use the filter delivery system for a jugular approach, the introducer sheath 200 is connected to the pusher assembly 325 at a jugular end 300F such that the extension elements of the filter 100 are introduced first. To facilitate the connection of the introducer sheath 200 to the pusher assembly 325, a bevel 224 may be provided at the ends 300F and 300J of the introducer sheath 200. The pusher assembly 325 seals to the femoral end 300F by locking to it. The introducer sheath 200 has a length that is preferably sufficient to extend from the access to the delivery location in either a femoral or jugular approach. The pusher assembly 325 may have a dilator as indicated figuratively at 333. A pusher 315 at the end of a shaft 320 is pushed through the pusher assembly 325 by a suitable manually-operated or automatic mechanism. Once the introducer sheath 200 is positioned with its distal end at the delivery site, the pusher 315 is advanced until it contacts the filter. The pusher 315 is finally pushed until the filter 100A is deployed. Preferably, removable seals are provided on the ends 300J and 300F of the introducer sheath 200 such that the introducer sheath houses and encloses the filter 100A in a sterile condition until the seals are removed in preparation for filter delivery. Note that the introducer sheath 200 can be made shorter than the length required to extend from the access to the vena cava if the deployment actuator is made suitably elongate to make up the difference.

In the foregoing embodiments, the introducer sheath may be a single-use article that is used to store the filter until it is used. The pusher assembly may also be a single-use disposable component. In an embodiment, the pusher assembly (e.g., 325) is packaged with the reversible introducer sheath and filter described above.

In use, a clinician may first determine whether to use a femoral or jugular approach. The introducer sheath 200 is unsealed and attached to the pusher assembly at the jugular or femoral end, according to the approach (femoral or jugular) selected. The introducer sheath 200 is then fed into the selected approach and the pusher assembly used to push the filter out of the introducer sheath.

While the introducer sheath 200 was described as being attachable to a deployment device using a snap-fit type mechanism, other types of attachments are possible. For example, a locking ring, swage fitting, threaded attachment, or slip ring type of attachment or even frictional engagement of mating sleeves could be used.

Also, while a particular example of a filter was shown, other kinds of filters may be used with the present delivery system. Preferably, the filter has a cranial end and a caudal end such that the system can be advantageously used to orient the filter simply by orienting the introducer sheath to the access and attaching the deployment device to the corresponding end. The engagement elements of the example filter included hooks which made it desirable to have a spline cap, but the spline cap may not be necessary depending on the particular configuration of the filter. For example, some types of engagement mechanisms will readily slide on the interior surface of the sheath. In addition, if hooks are provided on the filter, a circumferential jog may be formed into the legs to provide a portion that can ride on the rails of the sheath and thereby prevent the hooks from engaging the sheath interior surface.

In addition, while the deployment mechanism discussed above included a mechanical pusher, it is possible to employ a pneumatic or hydraulic pushing device or even a pulling mechanism for deployment. For example, a suture threaded around the end of the introducer sheath and back could be used to pull a filter out of a suitably designed sheath. Saline fluid could be used to flush a filter from the sheath. A piston driven by air pressure could also be used to push the filter.

While in the example embodiments of introducer sheath 200, the ends of the sheath 300J and 300F are configured as male fittings which are received by female mating fittings on the pusher assembly 325, other embodiments are possible. For example, the introducer sheath 200 could instead be provided with female fittings that mate with a male fitting on the pusher assembly 325. Also, the nature, size, and type of fitting used on the ends of the sheath 300J and 300F need not be identical in all embodiments. For example, as shown in FIG. 6, the same introducer sheath could have a small-diameter end 368 and a large diameter end 366 which are capable of mating to the same pusher assembly 372; the large-diameter end 366 fitting a large recess 371 and the small-diameter end 368 fitting a small recess 373.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

The invention claimed is:

1. An embolus filter delivery device for delivering an embolus filter to a delivery site within a human living host, comprising:
   a) a pusher assembly having a frame and a pusher member movable with respect to the frame, the pusher assembly having a pusher assembly end portion with a pusher assembly connector;
   b) an introducer sheath having an inner lumen and that is configured to be inserted into a circulatory system of a human living host, said sheath having first and second opposed sheath ends;
   c) first and second removable seals on the introducer sheath in a sheath initial position wherein the first seal is attached to the first sheath end and the second seal is attached to the second sheath end;
   d) an embolus filter housed in said lumen in between said sheath seals and ends in said sheath initial position, wherein in said sheath initial position the first sheath end has a first sheath end connector and the second sheath end has a second sheath end connector, each end connector enabling connection of a said sheath end to the pusher assembly frame at the pusher assembly connector;
   e) wherein in said sheath initial position either of said first and second sheath end connectors is selectively connectable to the pusher assembly connector;
   f) wherein a connection of the pusher assembly to the first sheath end enables the pusher member to push the filter out of the second sheath end;
   g) wherein in said sheath initial position each sheath end including said sheath end connector is sized and shaped to be insertable into the circulatory system of the human living host; and
   h) wherein when the pusher assembly and a selected sheath end of the first and second sheath ends are connected together and the sheath is inserted into the living host via jugular or femoral access, the other one of the sheath ends including a said sheath end connector is a free end that defines a discharge opening into the living host's circulatory system at a vena cava and enabling discharge and placement of the embolus filter at the vena cava of the living host.

2. The device of claim 1, wherein the introducer sheath has a length that is sufficient to extend from both a jugular access to a vena cava of a human and to extend from a femoral access to a vena cava of a human.

3. The device of claim 1, wherein the filter has a longitudinal axis and the filter has an asymmetric shape with respect to a line perpendicular to the longitudinal axis.

4. The device of claim 1, wherein the filter is configured to be pushed from either end by the pusher member.

5. The device of claim 1, further comprising a spline cap, the filter having engagement elements that are held by the spline cap.

6. The device of claim 1 further comprising a spline cap, the filter having engagement elements that are held by the spline cap, the spline cap being slidable within the introducer sheath.

7. The device of claim 1 further comprising a spline cap, the filter having engagement elements that are held by the spline cap, the spline cap being slidable within the introducer sheath, the introducer sheath having an internal surface with protruding portions that center the spline cap therewithin.

8. The device of claim 1 further comprising a spline cap, the filter having engagement elements with ends that are held by the spline cap, the spline cap being slidable within the introducer sheath, the introducer sheath having an internal surface with protruding portions that center the spline cap therewithin, the spline cap thus being centered thereby preventing the engagement element ends from contacting the internal surface.

9. The device of claim 1, further comprising a spline cap with grooves facing radially outward, the filter having engagement elements with ends that are held by the spline cap, the introducer sheath having an internal surface with protruding portions that engage the spline cap grooves to prevent the spline cap from rotating, thereby preventing the filter engagement elements from twisting.

10. The device of claim 1, wherein the filter has a hub and at least one corolla with axially and radially extending elements extending from the hub.

11. The device of claim 1, wherein the introducer sheath is sealed by said removable sheath seals at either end.

12. The device of claim 1, wherein the filter has ends that are oriented such that one end is aimed in the cranial direction when deployed in a vena cava and the other is aimed in the caudal direction when deployed in the vena cava.

13. A vena cava filter delivery system for delivery of the filter within a vena cava of a patient, comprising:
  a) a sheath having a cylindrically shaped outer surface, first and second cylindrically shaped sheath ends and an interior therebetween;
  b) a vena cava filter contained within said sheath interior, in an initial position wherein each sheath end is sealed so as to seal said vena cava filter within the interior;
  c) the filter and interior of the sheath being sterilized; and
  d) a delivery mechanism that can be selectively attached at a sheath end connection to a selected either of the first and second sheath ends with a delivery system attachment portion that is selectively connectable to either one of the sheath ends at the sheath end connection when the sheath is in the said initial position;
  e) wherein in said initial position the sheath and contained filter are configured to be deployed into a human patient's circulatory system;
  f) wherein the filter can be selectively deployed from one of the first and second sheath ends, the filter having a cranial end that is aligned with the sheath such that, when the filter is deployed, the cranial end faces the cranial end of the vena cava;
  g) wherein once connected to the delivery mechanism, either of the first and second sheath ends, the sheath and connection and contained filter are sized and shaped to be deployed into the human patient's circulatory system; and
  h) wherein when the delivery mechanism and a selected sheath end of the first and second sheath ends are connected together, and the sheath containing the filter in said initial position is deployed into the patient's circulatory system, the other one of the sheath ends including a said sheath end connection is a free end that defines a discharge opening into the patient's circulatory system at the vena cava, said free end discharge opening enabling discharge and placement of the filter at the vena cava of the patient.

14. The system of claim 13, wherein the sheath has a length that is sufficient to extend from both a jugular access to a vena cava of a human and to extend from a femoral access to a vena cava of a human.

15. The system of claim 13, wherein the filter has a longitudinal axis and the filter has an asymmetric shape with respect to a line perpendicular to the longitudinal axis.

16. The system of claim 13, further comprising a spline cap, the filter having engagement elements that are held by the spline cap.

17. The system of claim 13, further comprising a spline cap, the filter having engagement elements that are held by the spline cap, the spline cap being slidable within the sheath.

18. The system of claim 13, further comprising a spline cap, the filter having engagement elements that are held by the spline cap, the spline cap being slidable within the sheath, the sheath having an internal surface with protruding portions that center the spline cap therewithin.

19. The system of claim 13, further comprising a spline cap, the filter having engagement elements with ends that are held by the spline cap, the spline cap being slidable within the sheath, the sheath having an internal surface with protruding portions that center the spline cap therewithin, the spline cap thus being centered thereby preventing the engagement element ends from contacting the internal surface.

20. The system of claim 13 further comprising a spline cap with grooves facing radially outward, the filter having engagement elements with ends that are held by the spline cap, the introducer sheath having an internal surface with protruding portions that engage the spline cap grooves to prevent the spline cap from rotating, thereby preventing the filter engagement elements from twisting.

* * * * *